(12) United States Patent
Ingram et al.

(10) Patent No.: US 9,322,043 B2
(45) Date of Patent: Apr. 26, 2016

(54) METHODS OF USING CELLULASE FOR REDUCING THE VISCOSITY OF FEEDSTOCK

(75) Inventors: Lonnie O. Ingram, Gainesville, FL (US); Claudia C. Geddes, Raleigh, NC (US); James J. Peterson, Archer, FL (US); Michael T. Mullinnix, Gainesville, FL (US); Keelnatham Shanmugam, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 467 days.

(21) Appl. No.: 13/583,132

(22) PCT Filed: Mar. 10, 2011

(86) PCT No.: PCT/US2011/027923
§ 371 (c)(1),
(2), (4) Date: Dec. 17, 2012

(87) PCT Pub. No.: WO2011/112824
PCT Pub. Date: Sep. 15, 2011

(65) Prior Publication Data
US 2013/0098356 A1    Apr. 25, 2013

Related U.S. Application Data (60) Provisional application No. 61/312,636, filed on Mar. 10, 2010.

(51) Int. Cl.
*C12P 19/14* (2006.01)
*C12P 19/02* (2006.01)

(52) U.S. Cl.
CPC ............... *C12P 19/14* (2013.01); *C12P 19/02* (2013.01); *C12P 2203/00* (2013.01)

(58) Field of Classification Search
None
See application file for complete search history.

(56) References Cited

U.S. PATENT DOCUMENTS

| | | | |
|---|---|---|---|
| 5,720,971 A | 2/1998 | Beauchemin et al. | |
| 5,888,806 A * | 3/1999 | Nguyen | C12P 7/10 435/289.1 |
| 2005/0163880 A1 | 7/2005 | Pusateri et al. | |
| 2008/0102502 A1 * | 5/2008 | Foody | C12P 7/10 435/161 |

OTHER PUBLICATIONS

Rheology of Carboxymethyl Cellulose Solutions Treated With Cellulases. Jung Myoung Lee et al. 2006, BioResources 2(1), 20-33.*
Rheology of Carboxymethyl Cellulose Solutions Treated With Cellulases. By Jung Myoung Lee et al. 2006. NCSU. edu Bioresources. Submitted in IDS.*
"A New Approach to Measurement of Saccharifying Capacities of Crude Cellulase" By Wu et al. 2006. Bioresources 1(2): 189-200.*
International Search Report for corresponding International Application PCT/US2011/027923; Date of Mailing Jun. 9, 2011; (2 pages).
Written Opinion of the International Searching Authority for corresponding International Application PCT/US2011/027923.

* cited by examiner

*Primary Examiner* — Melvin C Mayes
*Assistant Examiner* — Colette Nguyen
(74) *Attorney, Agent, or Firm* — Saliwanchik, Lloyd & Eisenschenk (57) ABSTRACT

The invention provides methods for treatment of feedstock to reduce the relative viscosity and promote release of fermentable sugars.

25 Claims, 4 Drawing Sheets

METHODS OF USING CELLULASE FOR REDUCING THE VISCOSITY OF FEEDSTOCK

CROSS-REFERENCE TO RELATED APPLICATIONS

This application is the U.S. national phase, pursuant to 35 U.S.C. §371, of International application Ser. No. PCT/US2011/027923, filed Mar. 10, 2011, designating the United States and published in English on Sep. 15, 2011 as publication WO 2011/112824 A1, which claims priority to U.S. provisional application Ser. No. 61/312,636, filed Mar. 10, 2010. The entire contents of the aforementioned patent applications are incorporated herein by this reference.

STATEMENT REGARDING FEDERALLY SPONSORED RESEARCH

This work was supported by the U.S. Department of Energy, Grant number DE-FG36-08GO88142. The Government has certain rights in the invention.

BACKGROUND OF THE INVENTION

Lignocellulosic biomass (LCB) could serve as a primary carbohydrate feedstock to partially replace petroleum-based fuels and chemicals. LCB of terrestrial plants is composed of the thermoplastic lignin (15-25%) and two carbohydrate polymers, cellulose (35-50%) and hemicellulose (20-35%). Processes for depolymerization and fermentation of LCB are more complex and more capital intensive than established technologies for cornstarch or cane syrup. Unlike the starch, LCB has been designed by nature to serve as a structural element that resists microbial deconstruction. Pretreatments such as dilute mineral acids or base treatments are needed to render cellulose polymers accessible to enzymatic attack. Steam treatment with dilute mineral acids hydrolyzes hemicellulose into a pentose-rich syrup. This process is accompanied by side reactions and the production of inhibitors (furans, organic acids, and phenolics) that retard fermentation.

SUMMARY OF THE INVENTION

The invention provides methods for decreasing the relative viscosity of feedstock using chemical and enzymatic methods.

In one aspect, the invention generally provides a method of decreasing the relative viscosity of feedstock, the method involving incubating the feedstock with about 0.01 FPU to about 20 FPU cellulase/g dry weight of feedstock for about 10 minutes to about 10 hours at a pH of about 2 to about 6 and at a temperature of about 50° C. to about 70° C.; thereby decreasing the relative viscosity of the feedstock.

In another aspect, the invention provides a method of decreasing the relative viscosity of feedstock, the method involving incubating the feedstock with about 0.50 FPU to about 5 FPU cellulase/g dry weight of feedstock cellulase for about 15 minutes to about 2 hours; where the feedstock is incubated at a pH of 3 or less and at a temperature of at least 60° C.; thereby decreasing the relative viscosity of the feedstock, where the relative viscosity after treatment is less than 1500 cP.

In another aspect, the invention provides a method of reducing the viscosity of a feedstock having a viscosity of at least 20,000 cP involving combining the feedstock having a viscosity of at least 20,000 cP with a feedstock obtained by treating a feedstock by the method of any previous aspect, wherein the feedstock having a viscosity of at least 20,000 cP comprises 30% or less (e.g., 5%, 10%, 15%, 20%, 25%, 30%) of the volume of the feedstock treated by the method of any previous aspect.

In other embodiments of any of the above aspects, the feedstock is a bagasse, corn fiber, corn stover, a plant waste material, or a processing or agricultural byproduct. In other embodiments, the feedstock is a sugar cane, monoenergy cane, sorghum sudan, *Miscanthus*, switchgrass, wheat, milo, bulgher, barley, rice, corn, beet, or tree. In still other embodiments, prior to treatment, the feedstock has a relative viscosity of at least 20,000 cP. In various embodiments, the relative viscosity of the feedstock having a relative viscosity of at least 20,000 cP is reduced by at least 50%, 60%, 70%, 80%, 90%, 92%, 95%, 97%, 98%, or 99% as compared to the starting material. In other embodiments, the relative viscosity after treatment is less than 8000 cP, is less than 6000 cP, is less than 3000 cP, or is less than 1500 cP. In still other embodiments, the feedstock is incubated with about 0.05 FPU to about 20 FPU cellulase/g dry weight of feedstock (e.g., 0.05, 0.1, 0.25, 0.5, 1, 5, 10, 15, and 20), with about 0.50 FPU to about 5 FPU cellulase/g dry weight of feedstock, or with about 5 FPU to about 10 FPU cellulase/g dry weight of feedstock. In other embodiments, the feedstock is incubated for about 10 minutes to about 6 hours (e.g., 10, 15, 20, 25, 30, 35, 40, 45, 50, and 60 minutes and 1, 1.5, 2, 2.5, 3, 4, 5, and 6 hours). In other embodiments of any of the above aspects the feedstock is incubated for about 15 minutes to about 2 hours. In other embodiments, the pH is about 2 to about 6 (e.g., 2, 2.5, 3, 3.5, 4, 4.5, 5, 5.5, and 6), the pH is about 3 to about 6, the pH is about 2 to about 5, the pH is about 2 to about 4, or the pH is about 2 to about 3 (e.g., 2, 2.1, 2.2, 2.3, 2.4, 2.5, 2.6, 2.7, 2.8, 2.9, and 3). In still other embodiments, the feedstock is incubated at a temperature of 40° C. to 80° C. (e.g., 40, 50, 60, 70, and 80° C.), is incubated at a temperature of 45° C. to 80° C., is incubated at a temperature of 50° C. to 80° C., is incubated at a temperature of 50° C. to 75° C., or is incubated at a temperature at a temperature of 50° C. to 60° C. In still other embodiments, the feedstock is pretreated in an acidic solution prior to incubation with cellulase. In some embodiments, the acidic solution is phosphoric acid. In other embodiments, the acidic solution is sulfuric acid. The acidic solution contains about 0.01% to about 10% phosphoric acid (e.g., 0.01, 0.05, 0.1, 0.2, 0.25, 0.3, 0.4, 0.5, 0.6, 0.7, 0.8, 0.9, 1, 2, 3, 4, 5, 6, 7, 8, 9, and 10%), contains about 1% to about 8% phosphoric acid, or contains about 4% to about 6% phosphoric acid. In other embodiments, the acidic solution contains about 0.01% to about 10% sulfuric acid (e.g., 0.01, 0.05, 0.1, 0.2, 0.3, 0.4, 0.5, 0.6, 0.7, 0.8, 0.9, 1, 2, 3, 4, 5, 6, 7, 8, 9, and 10%), contains about 1% to about 8% sulfuric acid, or contains about 4% to about 6% sulfuric acid. In various embodiments, the feedstock is pretreated in an acidic solution for about 2 minutes to about 2 hours (e.g., 2, 3, 4, 5, 6, 7, 8, 9, 10, 15, 20, 30, 45, 60, and 120 minutes). In some embodiments, the feedstock is pretreated with heat, e.g., with steam, for about 1 hour to about 3 hours prior to treatment with cellulose (e.g., 1, 1.5, 2, 2.5, and 3 hours). In certain embodiments a treatment with steam is after a treatment with an acidic solution.

In other embodiments of any of the above aspects or of any other aspect of the invention delineated herein, prior to treatment, the feedstock contains a mixture of about 8-12% dry weight in an aqueous solution (e.g., 8, 8.5, 9, 9.5, 10, 10.5, 11, 11.5, and 12%). In various embodiments of any of the above aspects, the method extracts at least about 40%, 50%, 55%, 60%, or 65% of the fermentable sugars from the feedstock, where the fermentable sugars are one or more of xylose, galactose, and arabinose. In other embodiments, the amount of fermentation inhibitors extracted by the method is less than 1%, less than 0.75%, less than 0.5%, or less than 0.2% of the volume of the incubation mixture, where the fermentation inhibitors are one or more of furfural, hydroxymethylfurfural, formate, and acetate.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

FIGS. 1A-1D show the effect of phosphoric acid hydrolysate and cellulase enzyme loading on saccharification and relative viscosity. FIG. 1D shows the effect of incubation time on enzyme-solubilized sugars. Polynomial equations were developed that described saccharification. The decline in viscosity was modeled as a one phase exponential decay. Confidence limits (dashed lines) have been included for most curves ($p<0.05$). The thick continuous lines were generated using model equations. For saccharification, sugars present at zero time have been subtracted. Reported sugars were produced solely by enzymatic action.

FIG. 2 is a scatter plot of viscosity versus saccharification (10% w/w slurries of acid pretreated fiber in hemicellulose hydrolysate). Sugars present at zero time have been subtracted. Reported sugars were produced solely by enzymatic action. Dashed lines indicate the 95% confidence limits ($p<0.05$). The thick continuous line was generated using the model equation for a one phase exponential decay (Eq. 9). Flow through 12 mm diameter funnel stems was correlated with a viscosity of 3,000 cP or less.

FIGS. 3A and 3B show the effect of acid pretreated fiber additions on the viscosity of cellulase-digested slurries containing 10% dry weight acid pretreated fiber. Enzyme-digested slurries of acid pretreated fiber were prepared by incubating for (a) 2 h or (b) 6 h (Eqs. 10, 11 and 12) and cooled to room temperature to slow enzymatic action. These were mixed with 10% dry weight slurries of acid pretreated fiber that had not been treated with enzymes. Viscosities were measured immediately (within 1 min) These data were modeled as equations for sigmoid curves (Eqs. 10, 11 and 12), shown as thick black lines. Insufficient data points were available to model the 2-h treatment (FIG. 3a). Values connected with thin solid lines are within range of instrumentation (i.e. <20,000 cP). Curves derived from FIG. 1a were used to estimate the value at the immeasurable point for each curve and plotted as open symbols connected by a dashed arrow.

DEFINITIONS

"Bagasse" is the fibrous residue remaining after sugarcane or sorghum stalks are crushed to extract their juice.

As used herein, "centipoises" or "cP" is understood as a measurements of relative viscosity were used to compare slurries of pretreated bagasse following enzymatic digestion. Due to the nature of the material, a true cP value cannot be determined, however, a cP value for the purpose of comparison can be made. The values provided herein were made using a Brookfield DV-II+Pro Viscometer equipped with a T-bar (T-C spindle, 100 rpm). Although values are reported as centipoise (cP), these are only useful on a comparative basis between samples discussed herein, or between samples discussed herein with samples tested in a comparable manner. Characterization of the relative viscosity of a mixture herein is understood to include these limitations.

As used herein, a "percent decrease in relative viscosity" is understood as equaling 100%−(ending cP)/(starting cP) wherein the viscosity is measured by the methods provided herein. When the starting material is too viscous to be measured using the device provided herein, unless otherwise stated, the material is arbitrarily assigned a viscosity of 20,000 cP for the purpose of making the above calculation.

As used herein, "feedstock" is understood as any plant based material that can be converted through a chemical and/or mechanical processes into a substrate for ethanol production, e.g., fermentable sugars, by fermentation or other methods (e.g., enzymatic methods). Feedstock includes, but is not limited to a bagasse, corn fiber, corn stover, a plant waste material, a processing or agricultural byproduct, sugar cane, monoenergy cane, sorghum sudan, *Miscanthus*, switchgrass, wheat, milo, bulgher, barley, rice, corn, beet, or tree.

As used herein, "fermentation inhibitors" are naturally occurring products, e.g., acetate, furfural, and formate, that are produced in the process of converting a feedstock into a substrate for ethanol fermentation that decrease the efficiency of microbes or enzymes to convert the substrate for ethanol production into ethanol.

"Filter Paper Unit" or "FPU" as used herein is intended to be defined as set forth by IUPAC. Specifically, FPU is intended to mean the amount of enzyme in a 0.5 ml aliquot that results in a value of 2.0 mg of reducing sugar as glucose from 50 mg of filter paper (4% conversion) in 60 minutes.

As used herein, a "10% slurry" is understood to include about 8% to about 12% insoluble material per total volume.

Unless otherwise indicated, percent solutions or mixtures are understood to be weight/volume.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

"At least" a particular value is understood to mean the specific value provided, optionally including more.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

Any compositions or methods provided herein can be combined with one or more of any of the other compositions and methods provided herein.

DETAILED DESCRIPTION OF THE INVENTION

Options to consolidate bioprocessing steps with lignocellulose are limited in part by hydrolysate toxicity, material handling associated with fibrous suspensions, and the low activity of cellulase enzymes. Combinations of enzyme dose and treatment conditions provided herein were shown to improve flow properties and pumping of acid pretreated sugarcane bagasse slurries (10% dry weight). Low levels of cellulase enzyme (0.1 and 0.5 FPU/g dry weight acid pretreated bagasse) were found to reduce the viscosity of these slurries by 77-95% after 6 h of incubation. This coincided with solubilization of 3.5% of the bagasse dry weight. Flow of these slurries through small funnels was found to be an excellent predictor of success with centrifugal and diaphragm pumps. Equations were derived that describe changes in viscosity and solubilized sugars as a function of time and cellulase enzyme dosage.

When suspensions of fresh acid pretreated bagasse (10% dry weight) were blended with suspensions of acid pretreated bagasse (10% dry weight) that had been previously digested with cellulase enzymes (low viscosity), viscosity did not increase linearly. Viscosity of these mixtures remained relatively constant until a threshold level of fresh fiber was reached, followed by a rapid increase with further additions. Up to 35% of fresh acid pretreated bagasse could be blended with enzyme-digested fiber (5.0 FPU/g dry weight acid pretreated fiber; 6 h) with only a modest increase in viscosity. Without being bound by mechanism, a simple model is proposed to explain this phenomenon. The smooth surfaces of enzyme-treated fiber are proposed to hinder the frequency and extent of interactions between fibrils of fresh fiber particles (acid pretreated) until a threshold concentration is achieved, after which fiber interactions and viscosity increase dramatically. These results were used to model the viscosity in an ideal continuous stirred tank reactor (liquefaction) as a function of residence time and enzyme dosage.

Recent progress has been made in developing pretreatment conditions with phosphoric acid that minimize side products and more robust biocatalysts that have increased resistance to fermentation inhibitors such as furans. These improvements could facilitate the simultaneous fermentation of hemicellulose hydrolysate and cellulose-enriched fiber in a single vessel, avoiding a complex and costly liquid-solid separation. However, physical handling of LCB fiber suspensions remains a critical issue. Considerable bridging occurs among the fibers of sugarcane bagasse (dry solid or in an aqueous slurry; with or without acid pretreatment) that severely limits mixing and pumping. At 10% solids (dry weight) and higher, fibrous suspensions of acid pretreated bagasse trap most of the water and pour as a single tangled unit from a laboratory beaker. Warwick et al. (1985) reported that following mild acid treatment of lignocellulose, small molecules penetrate cell wall capillaries (spaces between microfibrils and cellulose molecules) in the amorphous regions. This external fibrillation greatly increases the water-holding capacity of LCB slurries by enhancing the abundance of capillary-like regions (external surface area) and potential bonding areas between fibrils and fibrils and water. Attempts to pump slurries containing 10% solids content or higher at pilot scale typically result in dewatering and blockage. Although it remains to be seen if this problem persists in very large commercial scale plants, mixing and pumping of LCB slurries represent significant challenges during pilot testing and scale-up.

Previous studies have investigated the effects of particle size on rheological properties of red-oak sawdust and the effect of initial solids loading on power consumption, glucose yield and rheological properties of dilute acid pretreated corn stover slurries. Decreasing the particle size of red-oak sawdust from 590-850 µm to 33-75 µm appeared to improve the efficiency of enzymatic saccharification by over 50% (i.e., conversion of cellulose to glucose) as well as reduce viscosities by as much as 98% using an initial solids concentration of 10% (w/w). A study by Rezania et al. (2009) reported that reducing the particle size of red-oak sawdust to <1 µm by sonication did not improve glucose release by cellulases and increased the viscosity. This increase in viscosity was proposed to result from dominant frictional effects at the tested particle size range.

Herein, the effects of cellulase treatments on the relative viscosity and flow properties of acid pretreated bagasse fiber (10% dry weight slurries in hemicellulose hydrolysate) without particle size reduction have been analyzed. Relative viscosity (single phase exponential decay) was correlated with the extent of saccharification under a wide range of conditions. These results were used to model viscosity changes in an ideal continuous stirred tank reactor with different amounts of cellulase.

As demonstrated herein, it was unexpected that low levels of cellulase enzymes were sufficient to reduce viscosity and improve the flow properties of acid pretreated bagasse slurries. Relationships between viscosity, cellulase dosage, incubation time, and saccharification were modeled and correlated with the ability of slurries to flow through graded funnels and be effectively pumped. Methods are provided to for decreasing viscosity at least 50%, 60%, 70%, 80%, 90%, 92%, 95%, 97%, 98%, or 99% as compared to the starting material, while extracting at least about 40%, 50%, 55%, 60%, or 65% of the sugars (e.g., xylose, galactose, and arabinose) from the feedstock and limiting production of fermentation inhibitors (less than 1%, less than 0.75%, less than 0.5%, or less than 0.2%). It was also unexpected that the addition of acid pretreated fiber slurries to enzyme digested (and acid pretreated) slurries had little effect on viscosity until a threshold concentration was reached, after which viscosity increased rapidly. A simple model was proposed to explain this phenomenon. Data from this study were used to model viscosity changes in an ideal continuous stirred tank reactor (CSTR).

Example 1

Materials and Methods

Materials

Sugarcane bagasse was provided by the Florida Crystals Corporation (Okeelanta, Fla.). Kerry Biocellulase W (164 mg protein/ml; approximately 50 filter paper units/ml) was provided by Kerry Biosciences (Cork, Ireland). Novozyme 188 β-glucosidase (approximately 277 cellobiase units/ml) was purchased from Sigma-Aldrich (St. Louis, Mo.). Thymol, phosphoric acid, and other chemicals were purchased from Thermo-Fisher Scientific (Waltham, Mass.).

Dilute Acid Pretreatment of Sugarcane Bagasse

Sugarcane bagasse was received at approximately 50% moisture. Bagasse was soaked in a 10-fold excess of 1% (w/w) phosphoric acid (2 h) and dewatered to 33% dry weight using a Centra CF basket centrifuge (International Equipment Company, Needham Heights, Mass.; 4 minutes at 3000 rpm). This acid-impregnated bagasse was autoclaved (500 g batches divided among three 1-L Pyrex beakers) at 145° C. (1 h), and cooled to room temperature. Sufficient deionized water was added to adjust the total weight to 3 kg (6 times the initial dry weight of untreated bagasse). The resulting slurry contained a total of 167 g/L acid pretreated bagasse fiber (approximately 112 g insoluble fiber/liter volume). After soaking and manual mixing to allow equilibration (2 h), most of the hydrolysate was removed by centrifugation. Resulting acid pretreated fiber (33% dry weight) and hemicellulose hydrolysate were stored at 4° C. Samples of acid pretreated fiber were washed with water prior to carbohydrate analysis.

Saccharification with Biocellulase W and β-Glucosidase

Saccharification of acid pretreated fiber was tested using Kerry Biocellulase W and Novozyme 188 β-glucosidase. Samples of acid pretreated fiber (20 g) were added to 500-ml flasks containing thymol (10 mg) as a preservative. Sufficient pH-adjusted hydrolysate (pH 3-8) containing Kerry Biocellulase W (0-5.0 FPU/g dry weight acid pretreated fiber) and Novozyme 188 β-glucosidase (0-3 cellobiose units/g dry weight acid pretreated fiber) was added to adjust the contents to 200 g (10% dry weight acid pretreated fiber). Most experiments were conducted at pH 5.0 (adjusted with 45% KOH) and 55° C.

Flasks with enzymes and acid pretreated fiber were incubated at 300 rpm (25-80° C.) for 1 h, and at 200 rpm thereafter. After adjustment for evaporative loss with deionized water, samples were removed and stored at −20° C. until analyzed. The extent of saccharification was measured as enzyme-solubilized sugar by the subtraction of sugars present before enzyme addition.

Relative Viscosity Measurement

Measurements of relative viscosity were used to compare rheological properties of acid pretreated fiber slurries following enzymatic digestion using a Brookfield DV-II+Pro Viscometer equipped with a T-bar (T-C spindle, 100 rpm). Although values are reported as centipoise (cP), these are only useful on a comparative basis. The non-Newtonian properties of this fibrous material preclude a more rigorous interpretation. Values ≥20,000 cP represent near immobilization of the spindle. The relative viscosity of water, acetate buffer and hemicellulose hydrolysate were also measured for comparison (approximately 1 cP for all).

Flow Properties Tests Using Graded Funnels

Plastic laboratory funnels with internal stem diameters 7 mm, 12 mm and 17 mm were used to compare the flow properties of acid pretreated fiber after the various treatments with Kerry Biocellulase W. Flow was assisted by gentle tapping. The slurries (10% dry weight acid pretreated fiber) were found to either pass through the funnel (indicated by a Y in Table 2) or to form a plug that resisted flow (indicated by an N).

Carbohydrate Composition and Analyses

Carbohydrate compositions of bagasse (as received), acid pretreated fiber and hemicellulose hydrolysate were determined as previously described (Geddes et al., 2010, incorporated herein by reference). Moisture content was measured using a Kern model MLB 50-3 moisture analyzer (Balingen, Germany) per manufacture's instructions. Sugars, organic acids and furans were measured by high-performance liquid chromatography (HPLC) using an Agilent Technologies 1200 series HPLC system (Santa Clara, Calif.) using routine methods.

Statistical Analysis

Graphpad Prism (Graphpad Software, San Diego, Calif.) was used to derive equations that simulate various relationships. This program was also used to perform two-way ANOVA (analysis of variance) of compositional analysis using the two-tailed student t-test. Differences in means were judged significant when P values for the null hypothesis were 0.05 or less.

Example 2

Composition

Bagasse samples were analyzed for carbohydrate composition over a 2-year period before and after acid pretreatment (1% phosphoric acid, 1 h, 145° C.). Sugar compositions are expressed as g/kg dry weight (Table 1). Steam pretreatment with dilute phosphoric acid-solubilized an average of 360 g/kg bagasse dry weight. Analysis of the acid pretreated fiber confirmed that the hemicellulose had been selectively solubilized. Differences in composition were judged significant for all sugars except galactose (p<0.05). As expected, glucan content of the insoluble fiber was increased by acid pretreatment. Due to the mild conditions used, approximately 19% of the xylose, 38% of the galactose and 15% of the arabinose remained associated with acid pretreated fiber.

Hemicellulose syrups were separated from acid pretreated fiber and also analyzed (Table 1). These contained 35 g/L total sugar and low concentrations of potential inhibitors of fermentation (4.6 g/L acetate, 0.5 g/L furfural and 0.3 g/L formate). Soluble sugars recovered in the hydrolysate represented 21% of the initial bagasse dry weight.

TABLE 1

Sugar composition of sugarcane bagasse, washed acid pretreated fiber and hemicellulose hydrolysate.

| Material | Glucose | Xylose | Galactose | Arabinose[a] | Total sugars |
|---|---|---|---|---|---|
| Bagasse as received[b] (g/kg) | 387 ± 20 | 212 ± 20 | 26 ± 11 | 34 ± 26 | 659 ± 40 |
| Washed fiber after pretreatment[c] (g/kg) | 593 ± 17 | 64 ± 19 | 15 ± 8 | 8 ± 10 | 680 ± 36 |
| Hemicellulose hydrolysate[d] (g/L) | 4 ± 1 | 27 ± 2 | 1 ± 1 | 3 ± 1 | 35 ± 2 |

[a] Arabinose may also include low levels of mannose and fructose which co-elute.
[b] mean ± SD (n = 14)
[c] mean ± SD (n = 18)
[d] Inhibitors present in hemicellulose hydrolysate included (g/L): furfural (0.49 ± 0.10), hydroxymethylfurfural (0.02 ± 0.04), formate (0.27 ± 0.04), and acetate (4.58 ± 0.23). An average of 36% of the bagasse dry weight was solubilized by acid pretreatment. mean ± SD (n = 54)

Example 3

Effect of Cellulase on Relative Viscosity

Figure 1A:
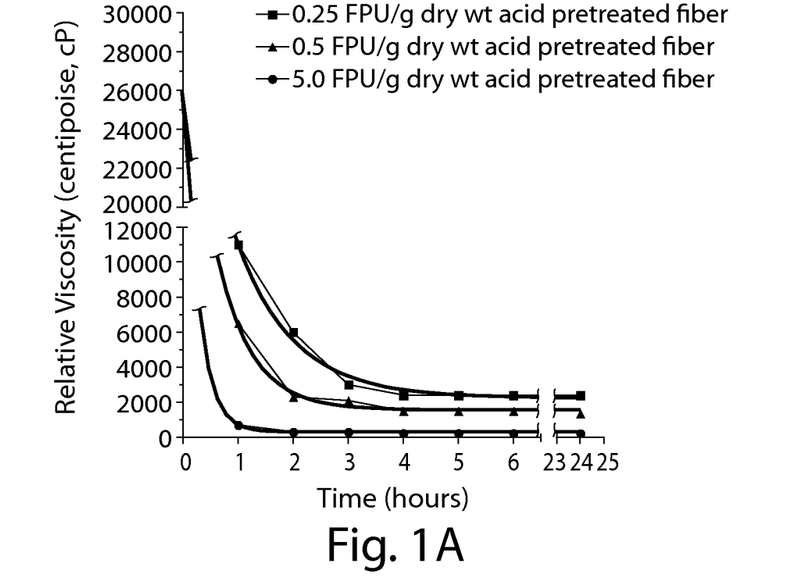
FIG. 1A shows the effect of incubation time on relative viscosity (Eqs. 1, 2 and 3).

The effect of incubation time on viscosity was examined using three cellulase enzyme loadings (0.25 FPU, 0.5 FPU and 5.0 FPU/g dry weight acid pretreated fiber). For the highest enzyme loading, the reduction in relative viscosity was nearly complete after only 1 h (FIG. 1a). Longer times were required for lower enzyme loadings. Relative viscosities declined to plateau values that were inversely proportional to the level of added cellulase, with no tendency to converge during longer incubation times. This plateau of relative viscosity with continued incubation is similar to saccharification but not well-understood (Warwick et al., 1985). The relationships between viscosity and incubation time for saccharification can be represented by a one phase exponential decay for each enzyme loading (FIG. 1a):

$$0.25 \text{FPU/g dry weight acid pretreated fiber}, \quad y = 23674e^{-0.978t} + 2196 \tag{1}$$

$$0.5 \text{FPU/g dry weight acid pretreated fiber}, \quad y = 24366e^{-1.592t} + 1504 \tag{2}$$

$$5.0 \text{FPU/g dry weight acid pretreated fiber}, \quad y = 25614e^{-4.050t} + 255.1 \tag{3}$$

For Eqs. (1)-(2), y represents the relative viscosity (cP) and t is incubation time (hours). R-squared values were calculated as 0.991, 0.989 and 0.975 for 0.25, 0.5 and 5.0 FPU/g dry weight acid pretreated fiber, respectively, indicating excellent agreement with experimental results. Confidence limits have been included for each curve ($p<0.05$).

Figure 1B:
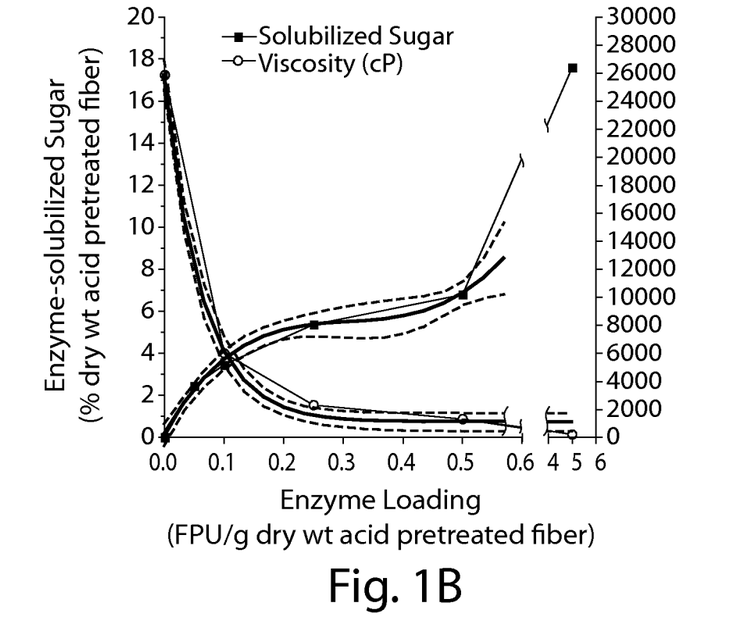
FIG. 1B shows the effect of enzyme loading on relative viscosity and saccharification (6 hour incubation; Eq. 4 and Eq. 5, respectively).

Acid pretreated fiber was slurried in hemicellulose hydrolysate to simulate process conditions in which solids and liquids were not separated. Acetate and phosphate present in the hydrolysate served as buffers for pH adjustment. Although the tangled mass of fiber is far from the ideal solutions described by viscosity theory, measurements of relative viscosity can provide useful information regarding changes in fluid properties. Preliminary experiments were conducted with a variety of cones, paddles and spindles. A small T-bar spindle was found to be the most useful. Slurries of hydrolysate containing 10% (w/w) acid pretreated fiber were digested with various levels of Biocellulase W (FIG. 1b). Temperature and pH optima for fungal cellulases (approximately pH 5.0 and 50° C.; Ou et al., 2009) were similar for Biocellulase W (pH 5.0 and 60° C.; Table 2). This demonstrates that cellulase from any of a number of sources can be used in the methods of the invention. Prior to enzyme addition, the T-bar was unable to rotate and registered values exceeding 20,000 cP. The extrapolated initial viscosity (t=0) value from FIG. 1a (i.e., 25,870 cP) was used as a maximum value in this graph. After 6 h incubation with Biocellulase W, relative viscosity was reduced by 77% with an enzyme loading of 0.1 FPU/g dry weight acid pretreated fiber, and by 95% with an enzyme loading of 0.5 FPU/g dry weight acid pretreated fiber. Previous studies have reported that rheological properties of cellulose derivatives are related to molecular structure parameters such as molar mass and particle size (Clasen et al., 2001; Gautier et al., 1991). Viscosity reduction can be accomplished by reducing the molar mass through enzymatic degradation of polysaccharide chains. Enzymatic treatment of biomass disrupts the interaction of fiber polymers such as cellulose chains creating smaller particles, which also decrease the viscosity. The relationship between enzyme loading and relative viscosity (6 h incubation) can be represented by a one phase exponential decay (FIG. 1b):

$$y = 247986e^{-15.75x} + 1049 \tag{4}$$

Here, y represents the relative viscosity in centipoise and x is enzyme loading (FPU/g dry weight acid pretreated fiber). The R-squared value was 0.9969, indicating a good fit with experimental results. Confidence limits have been included for each curve ($p<0.05$). With this equation the viscosity of the acid pretreated fiber slurry (10% solids) can be estimated for any enzyme loading (6 h incubation).

TABLE 2

Effects of cellulase enzymes on enzyme-solubilized sugars and rheological properties

| Cellulase levels (FPU/g dry weight) and incubation conditions | Treatment Time (h) | How Testing (funnel stem diameter in mm)* 2 7 | Enzyme-Solubilized Sugars (% dry weight acid pretreated fiber) | Relative Viscosity (cP) |
|---|---|---|---|---|
| Effect of Enzyme Loading (FPU/g dry weight acid pretreated fiber, pH 5, 55° C.) | .0 | 2 | | 0.0 ± 0.0 | >20000 |
| | .05 | 2 | | 1.8 ± 0.3 | >20000 |
| | .1 | 2 | | 2.0 ± 0.0 | >20000 |
| | .25 | 2 | | 4.1 ± 0.8 | 6000 |
| | .5 | 2 | | 4.9 ± 0.3 | 1500 |
| | .0 | 2 | | 12.9 ± 1.2 | 400 |
| | .0 | 6 | | 0.0 ± 0.0 | >20000 |
| | .05 | 6 | | 2.5 ± 0.0 | >20000 |
| | .1 | 6 | | 3.5 ± 0.2 | 6000 |
| | .25 | 6 | | 5.4 ± 0.4 | 2300 |
| | .5 | 6 | | 6.8 ± 0.1 | 1300 |
| | .0 | 6 | | 17.6 ± 0.4 | 200 |
| Effect of pH (55° C., 0.5 FPU/g dry weight acid pretreated fiber) | .0 | 2 | | 1.4 ± 0.1 | >20000 |
| | .0 | 2 | | 3.7 ± 0.2 | 7500 |
| | .0 | 2 | | 8.5 ± 3.4 | 1500 |
| | .5 | 2 | | ND | 2000 |
| | .0 | 2 | | 6.5 ± 1.6 | 6000 |
| | .5 | 2 | | ND | >20000 |
| | .0 | 2 | | 1.9 ± 0.5 | >20000 |
| | .0 | 2 | | 0.5 ± 0.6 | >20000 |
| | .0 | 6 | | 3.2 ± 0.1 | 5000 |
| | .0 | 6 | | 5.9 ± 0.1 | 1400 |
| | .0 | 6 | | 8.4 ± 2.1 | 500 |
| | .5 | 6 | D D D | ND | ND |
| | .0 | 6 | | 6.7 ± 0.1 | 600 |
| | .5 | 6 | D D D | ND | ND |
| | .0 | 6 | | 0.7 ± 0.4 | >20000 |
| | .0 | 6 | | 0.5 ± 0.4 | >20000 |
| Effect of Temperature (° C., pH 5, 0.5 FPU/g dry weight acid pretreated fiber) | 5 | 2 | | 0.9 ± 0.1 | >20000 |
| | 0 | 2 | | 2.3 ± 0.1 | 15000 |
| | 0 | 2 | | 3.6 ± 0.0 | 5000 |
| | 5 | 2 | | 4.9 ± 0.3 | 1500 |
| | 0 | 2 | | 5.8 ± 0.3 | 2000 |
| | 0 | 2 | | 4.5 ± 0.1 | >20000 |
| | 0 | 2 | | 1.0 ± 1.0 | >20000 |
| | 5 | 6 | | 1.4 ± 0.3 | >20000 |
| | 0 | 6 | | 4.1 ± 0.3 | 8000 |
| | 0 | 6 | | 7.5 ± 0.1 | 3000 |
| | 5 | 6 | | 11.8 ± 0.4 | 1700 |
| | 0 | 6 | D D D | ND | ND |
| | 0 | 6 | D D D | ND | ND |
| | 0 | 6 | | 2.0 ± 0.1 | >20000 |

*The N, Y and ND indicate no flow through the funnel, flow through the funnel, and data that was not determined respectively.

Example 4

Effect of Cellulase Loading on Extent of Saccharification

Figure 1C:
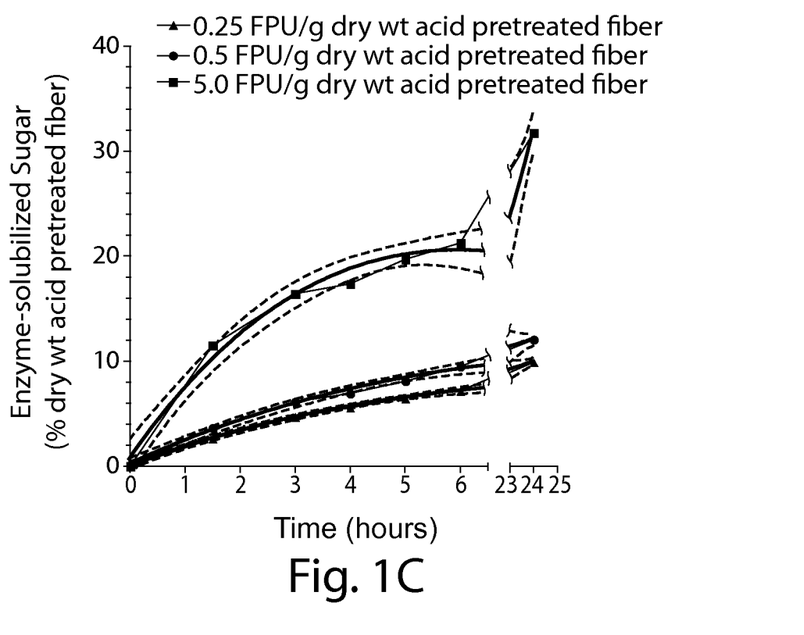
FIG. 1C shows the effect of incubation time on saccharification (Eqs. 6, 7 and 8).
Figure 1D:
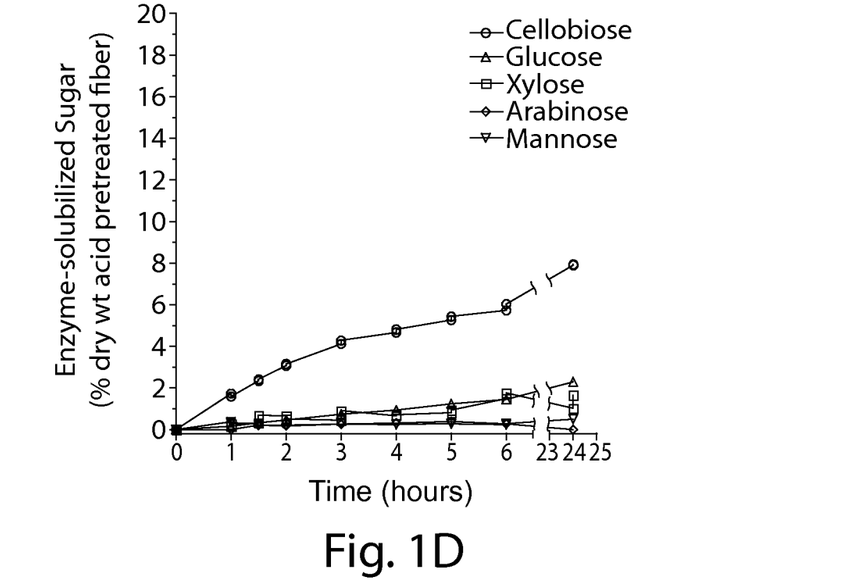

Surprisingly little saccharification was required to reduce viscosity (FIGS. 1b, 1c, and 1d). After 6 h, a very low enzyme loading of 0.1 FPU/g dry weight acid pretreated fiber (3.5% of the fiber dry weight solubilized) reduced relative viscosity by 77% (FIG. 1b). With 5.0 FPU/g dry weight acid pretreated fiber (6 h), viscosity was reduced by 99% accompanied by the saccharification of 17.6% of the dry weight. The relationship between enzyme loading and saccharification (FIG. 1b) and the time course for saccharification (FIG. 1c) can be represented by a fourth and third order polynomials, respectively. Confidence limits have been included for each curve (p<0.05).

Extent of saccharification versus enzyme loading (6 h incubation; FIG. 1b):

$$y=0.09071+49.80x-161.9x^2+194.7x^3-32.84x^4 \quad (5)$$

In this equation, y represents the amount of solubilized sugars (% dry weight acid pretreated fiber) and x is enzyme loading as FPU/g dry weight acid pretreated fiber. The R-squared value is 0.9980, indicating an excellent agreement with experimental results. The enzyme loading required for a desired sugar concentration (6 h of incubation) can be estimated using Eq. (5).

Extent of saccharification versus time using 5.0 FPU/g dry weight acid pretreated fiber (24 h; FIG. 1c):

$$y=0.6496+7.520t-0.8492t^2+0.02458t^3 \quad (6)$$

Extent of saccharification versus time using 0.5 FPU/g dry weight acid pretreated fiber (24 h; FIG. 1c):

$$y=0.1498+2.414t-0.1735t^2+0.003901t^3 \quad (7)$$

Extent of saccharification versus time using 0.25 FPU/g dry weight acid pretreated fiber (24 h; FIG. 1c):

$$y=0.01837+1.939t-0.1452t^2+0.003399t^3 \quad (8)$$

For Eqs. (6)-(8), y represents the amount of enzyme-solubilized sugars (% dry weight acid pretreated fiber) and t is time of enzymatic saccharification (hours). The R-squared values are 0.99 for all three enzyme loadings (5.0, 0.5, and 0.25 FPU/g dry weight acid pretreated fiber), indicating excellent agreement with experimental results. Using these equations, the amount of sugar that will be solubilized by a specified enzyme loading and incubation time (≤24 h) can be estimated. Similar trends were observed for individual sugars (FIG. 1d). Under the mild treatment conditions used, part of the hemicellulose remained associated with the fiber (Table 1). This hemicellulose was solubilized during incubation with Biocellulase W consistent with the presence of additional enzymatic activities (FIG. 1d). Curves defining individual sugars were not modeled.

Example 5

Effect of Enzyme Treatment on Flow Through Graded Funnels

The handling and transferring of fibrous slurries represent significant challenges for LCB conversion to fuels and chemicals. We have used three different funnels with internal stem diameters of 7 mm, 12 mm and 17 mm to compare the flow properties of acid pretreated fiber slurries (10% w/w). Flow was tested before and after enzyme treatments (Table 2). Acid pretreated fiber slurries failed to flow through all funnels prior to enzyme treatment. After 2 h of incubation, all enzyme concentrations allowed the fiber slurries to flow through the 17 mm stem even though viscosity measurements were above the measurable range (≥20,000 cP) in some cases. Only the two highest enzyme concentrations (0.5 and 5.0 FPU/g dry weight acid pretreated fiber) permitted flow through the 12 mm stem. None permitted flow through the 7 mm stem (2 h).

After 6 h of incubation, the highest enzyme concentration permitted flow through the 7 mm stem. Flow properties followed the same trends (pH, temperature, enzyme dosage, time) observed for relative viscosity in most cases, and were improved by greater saccharification and longer incubation times. Flow through the 17 mm, 12 mm and 7 mm stems occurred at relative viscosities of ≥20,000 cP, ≤3,000 cP and ≤200 cP, respectively. These corresponded to the saccharification of approximately 1%, 5% and 17% of acid pretreated fiber.

More practical tests were conducted with acid and enzyme treated bagasse using a centrifugal pump (Jabsco, White Plains, N.Y.; Model 18690-0000,115 V; 7.2 AMPS; 1½ in. inlet diameter, ¾ in outlet) and a pneumatic diaphragm pump (IDEX Aodd Inc., Mansfield, Ohio; Sandpiper Model SIF Metallic Design Level 1; 1 in. inlet and outlet diameter). Positive results for flow through the 12 mm funnel stem were found to be an excellent predictor of successful pumping. Enzyme dose and treatment conditions can be used in combination to improve flow properties and pumping of acid pretreated sugarcane bagasse.

Example 6

Correlation Between Extent of Saccharification and Relative Viscosity

Figure 2:
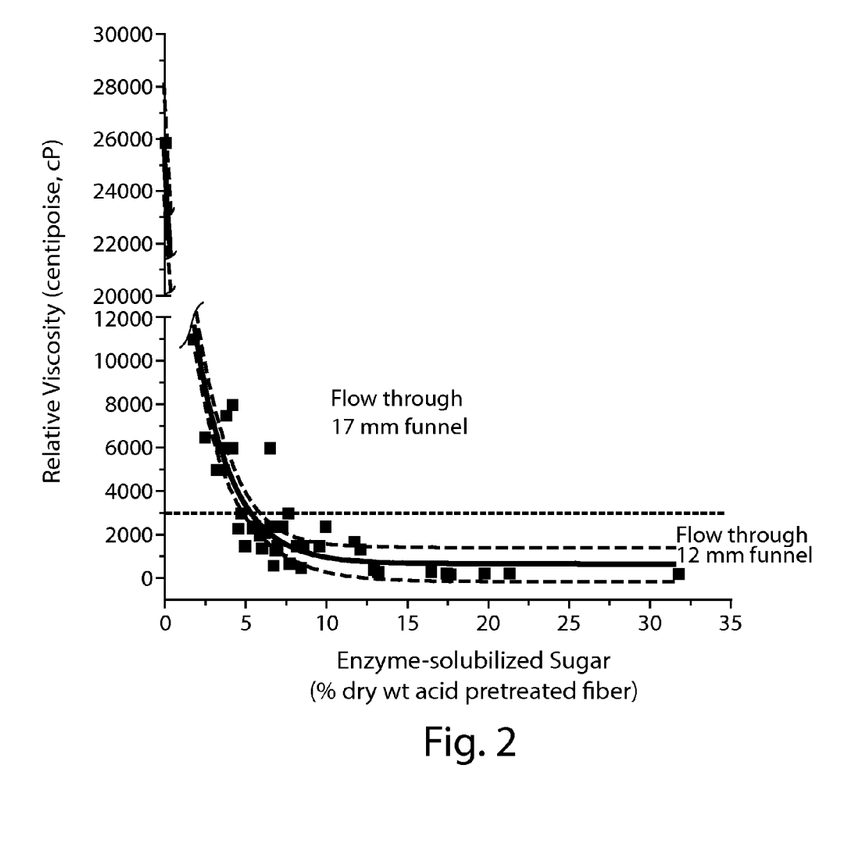

Extent of saccharification and relative viscosity were measured under a variety of conditions using six independent samples of bagasse. This data has been assembled into a scatter plot (FIG. 2). Relative viscosity was dramatically reduced by a small amount of saccharification. With 5% saccharification, relative viscosity was reduced by almost 90%. However, saccharification of 20-30% of the dry weight was required to achieve the lowest viscosity. An equation was developed to model this data (FIG. 2).

The decline in viscosity during saccharification was represented by a one phase exponential decay (R-squared=0.9316). Confidence limits were also included (p<0.05). Eq. (9) can be used to estimate the viscosity of the slurry based on enzyme-solubilized sugar, a property that can be correlated with pumping (Table 2).

$$y=25319e^{-0.4412x}+592.2 \quad (9)$$

In this equation, y represents the relative viscosity in centipoise and x is solubilized sugar as a percentage of acid pretreated fiber. A relative viscosity of 3,000 cP or less was needed for flow through a funnel with a 12 mm ID stem (Table 2) and is indicated by a horizontal dashed line on FIG. 2. Reduction of viscosity to this level required the solubilization of at least 50 g sugar/kg acid pretreated fiber.

Example 7

Effect of Blending Acid Pretreated Fiber (No Enzyme Digestion) with Enzyme-Digested Acid Pretreated Fiber (pH 5.0, 55° C., 6 h) on Viscosity The physical appearance of acid pretreated fiber slurries was dramatically altered by enzyme treatments. Initially, slurries with 10% fiber occupied the entire volume, poured as a single tangled unit and failed to settle indicating extensive bridging and strong interactions between fibers or between fibers and water. After enzyme digestion, slurries readily settled and behaved as a suspension of independent particles with lower viscosities.

Figure 3A:
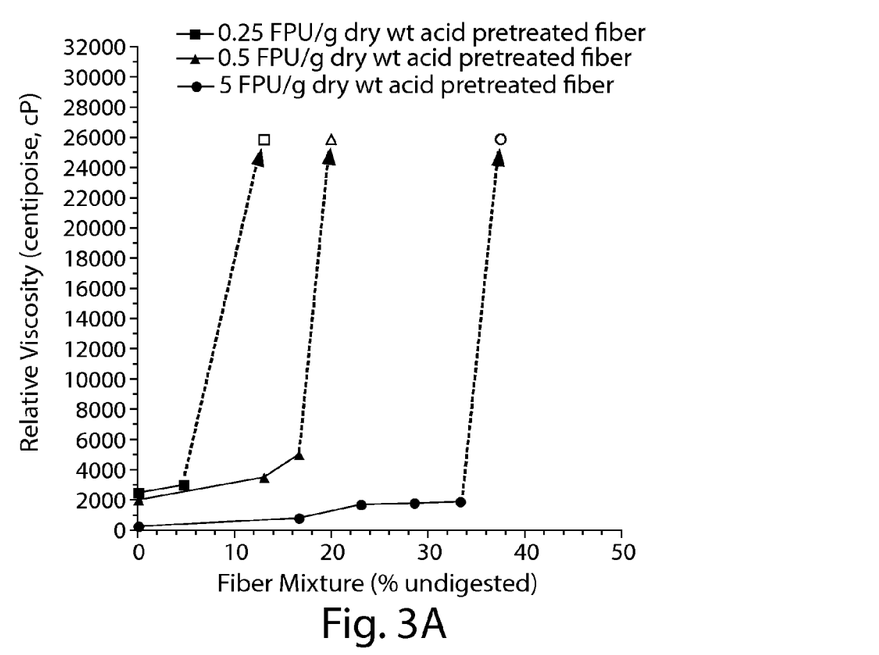
Figure 3B:
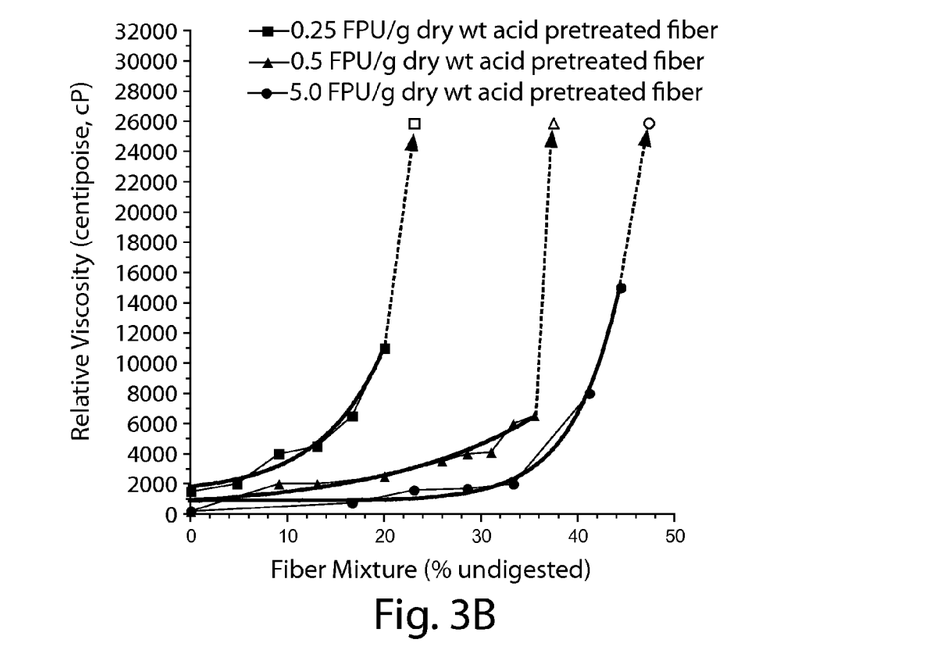

Additional experiments were conducted to determine the effect of combining enzyme-digested slurries of acid pretreated fiber and undigested slurries on the relative viscosity of the mixture (FIG. 3). Acid pretreated fiber slurries (10% dry weight fiber in hydrolysate) were digested for 2 h (FIG. 3a) or 6 h (FIG. 3b) using different amounts of Biocellulase W (5.0, 0.5, and 0.25 FPU/g dry weight acid pretreated fiber) and cooled to room temperature to minimize further enzyme action. Relative viscosity was measured immediately after mixing (within 1 min) with various amounts of acid pretreated fiber (no enzyme treatment). Relative viscosities of all enzyme treated bagasse were low (200-2,500 cP) in comparison to undigested material (≥20,000 cP). Addition of small amounts of acid pretreated fiber (no enzyme digestion) had little effect on relative viscosity until a threshold concentration was reached (FIG. 3). At this point, further addition of acid pretreated fiber resulted in an abrupt increase in viscosity. The proportion of acid pretreated fiber (no enzyme digestion) that could be accommodated below each threshold value varied considerably (5-35%) and was directly related to the initial viscosity of enzyme-digested bagasse. Using 3,000 cP as a conservative maximum for pumping based on funnel experiments (12 mm stem), up to 35% fresh acid pretreated fiber could be blended with enzyme-digested acid pretreated fiber (5.0 FPU/g dry weight acid pretreated fiber; 6 h). At one-tenth this enzyme loading, up to 23% undigested acid pretreated fiber could be accommodated. At 0.25 FPU/g dry weight acid pretreated fiber cellulase loadings, the addition of more than 5% to 6% undigested acid pretreated fiber resulted in a dramatic rise in viscosity. The relationship between acid pretreated fiber additions (fresh) to enzyme-digested fiber and relative viscosity can each be represented by equations (10)-(12) sigmoidal curves) for each level of enzyme (FIG. 3b).

0.25 FPU/g dry weight acid pretreated fiber (6 h incubation):

$$y = 1324 + \frac{874046}{1 + 10^{(3.30-0.067x)}} \quad (10)$$

0.5 FPU/g dry weight acid pretreated fiber (6 h incubation):

$$y = 224.3 + \frac{313535.7}{1 + 10^{(2.70-0.028x)}} \quad (11)$$

5.0 FPU/g dry weight acid pretreated fiber (6 h incubation):

$$y = 811.6 + \frac{645898.4}{1 + 10^{(5.67-0.091x)}} \quad (12)$$

In Eqs. (10)-(12), y represents the relative viscosity (cP) and x is the fraction of undigested fiber as a percentage of total (10% dry weight). The R— squared values are 0.9795, 0.9461 and 0.9946 for the equations above respectively, indicating excellent agreement with experimental results. The large confidence limits for sigmoidal curves obscured the curves and were omitted. Two-hour treatments were judged to have too few data plots to develop a model (FIG. 3a).

These data indicate that acid pretreated fiber that has been partially digested with enzymes has the ability to accommodate or passivate additions of fresh acid pretreated fiber (no cellulase treatment; up to 30% of total fiber) with little increase in viscosity. Without being bound by mechanism, this observation, together with the rapid decline in viscosity resulting from limited saccharification suggests a simple mechanism. It is suggested that the viscosity of acid pretreated fiber is proposed to result from the tangling interactions of surface-exposed micro-fibers as observed previously and the bonding between fibrils and water (water-holding capacity) in the amorphous regions of fibers. Digesting these small fibers with enzymes provides a smooth surface, reducing viscosity with limited saccharification. These smooth enzyme-treated particles would also serve as a diluent that physically hinders associations between small fibers on the surface of fresh acid pretreated fiber (no enzymes) until the threshold concentration for random associations is reached leading to increased viscosity (FIG. 3).

Example 8

Modeling an Ideal Continuous Stirred Tank Reactor (CSTR) to Decrease Viscosity

We have used the experimental data (FIGS. 2 and 3) to estimate the upper bound viscosity of an ideal CSTR for liquefaction at different mean residence times (r). The residence time distribution (RTD) of the reactor is a probability function describing the length of time the fluid elements of the tank spend inside the reactor. The ideal CSTR assumes that the material at the inlet is instantly and completely mixed into the bulk material of the reactor and that the contents of the reactor have the same composition as the outlet at all times. The ideal CSTR has an exponential residence time distribution (E(t); Fogler, 1986):

$$E(t) = \frac{1}{\tau}e^{-t/\tau} \quad (13)$$

Here $\tau$ represents the mean residence time, defined by $\tau=V/Q$ where V is the volume of the tank and Q is the inlet volumetric flow rate, and $\tau$ represents residence time. The fraction of the reactor contents that has a retention time between t and t+dt inside the reactor is given by E(t)dt. The fraction of the reactor contents that has a retention time less than $t_1$ and greater than $t_1$ are given by Eqs. (14) and (15) respectively (Fogler, 1986).

$$\int_0^{t_1} E(t)dt \quad (14)$$

$$\int_{t_1}^{\infty} E(t)dt = 1 - \int_0^{t_1} E(t)dt \quad (15)$$

Using Eqs. (13)-(15) above, the fraction wi of the reactor contents with a residence time t such that $i\Delta t \leq t < (i+1)\Delta t$ can be expressed as:

$$w_i = \left(1 - e^{\frac{-\Delta t}{\tau}}\right) * e^{\frac{-i\Delta t}{\tau}} \quad (16)$$

If we make the assumption that viscosity is additive, then the viscosity ($\mu$) of the reactor contents can be expressed in terms of the viscosity $\mu_i$ of fraction i:

$$\mu = \sum_{i=0}^{\infty} w_i \mu_i \quad (17)$$

However, when FIG. 3's data is plotted with Eq. (17) for each enzyme loading, the experimental data fall below the linear viscosity curve (Eq. 17) until a maximum viscosity value, μmax, is reached:

$$\mu \leq \sum_{i=0}^{\infty} w_i \mu_i \text{ if } \mu < \mu_{max} \quad (18)$$

From Eqs. (1)-(3) we obtain:

$$\mu_i = a + be^{-ic\Delta t} \quad (19)$$

where a, b, and c are constants derived from the best fit model of the experimental data (FIG. 1a) for each enzyme loading using the constraint that the initial viscosity for undigested material at t=0 is the same for all three enzyme loadings. This constraint allowed the derivation of a relative viscosity value (i.e. 25,870 cP) for undigested material, which was not measurable with the instrumentation but could be used to model an ideal CSTR.

By substituting Eq. (19) for μi and Eq. (16) for wi into Eq. (18) we obtain:

$$\mu \leq \sum_{i=0}^{i=\infty} \left( (a + be^{-ic\Delta t}) * \left(1 - e^{\frac{-\Delta t}{\tau}}\right) * e^{\frac{-i\Delta t}{\tau}} \right) \quad (20)$$

which can be expressed as:

$$\mu \leq a + b \frac{1 - e^{\frac{-\Delta t}{\tau}}}{1 - e^{-(c + \frac{1}{\tau})\Delta t}} \quad (21)$$

Taking the limit Δt→0 we get 0/0, so we can use L'Hopital's Rule:

$$\mu \leq a + b \lim_{\Delta t \to 0} \frac{-e^{\frac{-\Delta t}{\tau}} * \left(-\frac{1}{\tau}\right)}{-e^{-(c+\frac{1}{\tau})\Delta t} * \left(-\left(c + \frac{1}{\tau}\right)\right)} \quad (22)$$

$$\Rightarrow \mu \leq a + \frac{b}{1 + c\tau} \quad (23)$$

Eq. (23) can be used to estimate an upper bound viscosity in a CSTR with a specific residence time and enzyme loading when the viscosity falls below a certain μmax. The maximum viscosities we could establish an upper bound for (i.e. μmax) at each enzyme loading were determined graphically by transposing Eq. (17) with Eqs. (10)-(12) and were 5,500 cP, 12,000 cP, and 11,200 cP for 0.25 FPU, 0.5 FPU, and 5 FPU respectively. Predicted upper bound values for viscosity are given in Table 3. From this model, the predicted mean residence times to produce a slurry that can be pumped (i.e., viscosity≤3,000 cP) are 30 h, 9 h, and 2 h for 0.25 FPU, 0.5 FPU, and 5 FPU respectively.

TABLE 3

Predicted upper bound viscosity for an ideal continuous stirred tank reactor (CSTR).

| Enzyme loading (FPU/g fiber) | Viscosity at different mean residence times (τ, hours) | | | | | | | | | | | | |
|---|---|---|---|---|---|---|---|---|---|---|---|---|---|
| | 0.5 | 1 | 2 | 3 | 4 | 5 | 6 | 7 | 8 | 9 | 10 | 20 | 30 |
| 0.25 | *18096* | *14166* | *10206* | 8214 | 7016 | 6216 | 5643 | 5213 | 4879 | 4611 | 4392 | 3347 | 2976 |
| 0.50 | *15069* | 10903 | 7326 | 5721 | 4810 | 4222 | 3812 | 3510 | 3277 | 3093 | 2943 | 2245 | 2003 |
| 5.00 | 8723 | 5327 | 3069 | 2203 | 1744 | 1461 | 1268 | 1128 | 1022 | 939 | 872 | 568 | 464 |

Note:
Italicized values are above the confidence limit (i.e. viscosity > $\mu_{max}$) and therefore cannot be used as upper bound viscosity predictions.

REFERENCES

Chandra, R. P., Bura, R., Mabee, W. E., Berlin, A., Pan, X., Saddler, J. N., 2007. Substrate pretreatment: the key to effective enzymatic hydrolysis of lignocellulosics? Adv. Biochem. Engin./Biotechnol. 108, 67-93.

Clasen, C., Kulicke, W. M., 2001. Determination of viscoelastic and rheo-optical material functions of water-soluble cellulose derivatives. Prog. Polym. Sci. 26, 1839-1919.

Dasari, R. K., Dunaway, K., Berson, E. R., 2009. A scraped surface bioreactor for enzymatic saccharification of pretreated corn stover slurries. Energy & Fuels 23, 492-497.

Dasari, R. K., Berson, R. E., 2007. The effect of particle size on hydrolysis reaction rates and rheological properties in cellulosic slurries. Appl. Biochem. Biotechnol. 136-140, 289-299.

Demirbas, A., 2005. Bioethanol from cellulosic materials: a renewable motor fuel from biomass. Energy Sources 27, 327-337.

Fogler, H. S., 1986. Distributions of residence times for chemical reactors, in: Elements of chemical reaction engineering. Prentice Hall, New Jersey, pp. 629-679.

Gautier, S., Lecourtler, J., 1991. Structural characterization by $^{13}C$ nuclear magnetic resonance of hydrolysed carboxymethylcellulose. Polym. Bulletin 26, 457-464.

Geddes, C. C., Peterson, J. J., Roslander, C., Zacchi, G., Mullinnix, M. T., Shanmugam, K. T., Ingram, L. O., 2010. Optimizing the saccharification of sugar cane bagasse using dilute phosphoric acid followed by fungal cellulases. Bioresour. Technol. 101, 1851-1857.

Hahn-Hagerdal, B., Galbe, M., Gorwa-Grauslund, M. F., Liden, G., Zacchi, G., 2006. Bio-ethanol-the fuel of tomorrow from the residues of today. Trends Biotechnol. 24, 549-556.

Heer, D., Heine, D., Sauer, U., 2009. Resistance of *Saccharomyces cerevisiae* to high furfural concentration is based on NADPH-dependent reduction by at least two oxidoreductases. Appl. Environ. Microbiol. 75, 7631-7638.

Ingram, L. O., Aldrich, H. C., Borges, A. C. C., Causey, T. B., Martinez, A., Morales, F., Saleh, A., Underwood, S. A., Yomano, L. P., York, S. W., Zaldivar, J., Zhou, S., 1999. Enteric bacterial catalysts for fuel ethanol production. Biotechnol. Prog. 15, 855-866.

Ingram, L. O., Lai, X., Moniruzzaman, M., Wood, B. E., York, S. W., 1997. Fuel ethanol production from lignocellulose using engineered bacteria. In: Saha, B. H., Woodward, J. (Eds.), Fuel and chemicals from biomass. American Chemical Society, Washington, D.C., pp. 57-73.

Jeffries, T. W., 1994. Biodegradation of lignin and hemicelluloses. In: Ratledge, C. (Ed.), Biochemistry of microbial degradation. Kluwer Academic Publishers, Dordrecht, Netherlands, pp. 233-277.

Liu, Z. L., Ma, M., Song, M., 2009. Evolutionarily engineered ethanologenic yeast detoxifies lignocellulosic biomass conversion inhibitors by reprogrammed pathways. Mol. Genet. Gen. 282, 233-244.

Miller, E. N., Jarboe, L. R., Yomano, L. P., York, S. W., Shanmugam, K. T., Ingram, L. O., 2009a. Silencing of NADPH-dependent oxidoreductase genes (yqhD and dkgA) in furfural-resistant ethanologenic *Escherichia coli*. Appl. Environ. Microbiol. 75(13), 4315-4323.

Miller, E. N., Jarboe, L. R., Turner, P. C., Pharkya, P., Yomano, L. P., York, S. W., Nunn, D., Shanmugam, K. T., Ingram, L. O., 2009b. Furfural inhibits growth by limiting sulfur assimilation in ethanologenic *Escherichia coli* strain LY180. Appl. Environ. Microbiol. 75(19), 6132-6141.

Mosier, N., Wyman, C., Dale, B., Elander, R., Lee, Y. Y., Holtzapple, M., Ladisch, M., 2005. Features of promising technologies for pretreatment of lignocellulosic biomass. Bioresour. Technol. 96, 673-686.

Ohgren, K., Bura, R., Saddler, J., Zacchi, G., 2007. Effect of hemicellulose and lignin removal on enzymatic hydrolysis of steam pretreated corn stover. Bioresour. Technol. 98, 2503-2510.

Ou, M S, Mohammed, N, Ingram, L O, Shanmugam, K T, 2009. Thermophilic *Bacillus coagulans* requires less cellulases for simultaneous saccharification and fermentation of cellulose to products than mesophilic microbial biocatalysts. Appl Biochem Biotech 155, 379-385.

Overend, R. P., Chornet, E., 1987. Fractionation of lignocellulosics by steam-aqueous pretreatments. Philos. Trans. Royal Soc. Lond. A 321, 523-536.

Palmqvist, E., Hahn-Hagerdal, B., 2000a. Fermentation of lignocellulosics hydrolysates. I: Inhibition and detoxification. Bioresour. Technol. 74, 17-24.

Palmqvist, E., Hahn-Hagerdal, B., 2000b. Fermentation of lignocellulosics hydrolysates. II: Inhibitors and mechanisms of inhibition. Bioresour. Technol. 74, 25-33.

Rezania, S., Zhuoliang, Y., Berson, R. E., 2009. Enzymatic saccharification and viscosity of sawdust slurries following ultrasonic particle size reduction. Appl. Biochem. Biotechnol. 153, 103-115.

Warwick, L. M., Gray, P. P., Mandels, M., 1985. Enzymatic hydrolysis of cellulose in lignocellulosic materials. Crit. Rev. Biotechnol. 3(3), 235-276.

Wood, B. E., Aldrich, H. C., Ingram, L. O., 1997. Ultrasound stimulates ethanol production during the simultaneous saccharification and fermentation of mixed waste office paper. Biotechnol. Prog. 13(3), 232-237.

Zaldivar, J., Ingram, L. O., 1999a. Effect of selected aldehydes on the growth and fermentation of ethanologenic *Escherichia coli*. Biotechnol. Bioeng. 65, 24-33.

Zaldivar, J., Ingram, L. O., 1999b. Effect of organic acids on the growth and fermentation of ethanologenic *Escherichia coli* LY01. Biotechnol. Bioeng. 66, 203-210.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of decreasing the relative viscosity of feedstock comprising:
    incubating the feedstock with about 0.01 FPU to about 20 FPU cellulase/g dry weight of feedstock for about 10 minutes to about 10 hours at a pH of about 2 to about 6 at a temperature of about 40° C. to about 80° C., said feedstock, prior to treatment, having a relative viscosity of at least 20,000 cP;
    thereby decreasing the relative viscosity of the feedstock.

2. The method of claim 1, wherein the feedstock is a bagasse, corn fiber, corn stover, a plant waste material, a processing or agricultural byproduct, a sugar cane, monoenergy cane, sorghum sudan, *Miscanthus*, switchgrass, wheat, milo, bulgher, barley, rice, corn, beet, or tree.

3. The method of claim 1, wherein the feedstock is incubated with about 0.05 FPU to about 20 FPU cellulase/g dry weight of feedstock.

4. The method of claim 1, wherein the feedstock is incubated for about 10 minutes to about 6 hours.

5. The method of claim 1, wherein the relative viscosity after treatment is less than 8000 cP.

6. The method of claim 1, wherein the pH is about 3 to 6.

7. The method of claim 6, wherein the feedstock is incubated for about 10 minutes to about 6 hours.

8. The method of claim 6, wherein the relative viscosity after treatment is less than 8000 cP.

9. The method of claim 1, wherein the feedstock is incubated at a temperature of: about 45° C. to about 80° C.

10. The method of claim 9, wherein the feedstock is incubated for about 10 minutes to about 6 hours.

11. The method of claim 9, wherein the relative viscosity after treatment is: less than 8000 cP.

12. The method of claim 1, wherein the feedstock is pretreated in an acidic solution prior to incubation with cellulase.

13. The method of claim 12, wherein the acidic solution is phosphoric acid or sulfuric acid.

14. The method of claim 13, wherein the phosphoric acid solution comprises about 0.01% (w/w) to about 10% (w/w) phosphoric acid.

15. The method of claim 13, wherein the sulfuric acid solution comprises about 0.01% (w/w) to about 10% (w/w) sulfuric acid.

16. The method of claim 12, wherein the feedstock is pretreated in an acidic solution for about 2 minutes to about 2 hours.

17. The method of claim 1, wherein the feedstock is pretreated with steam for about 1 hour to about 3 hours prior to treatment with cellulase.

18. The method of claim 17, wherein the feedstock is treated with steam after treatment with an acidic solution.

19. The method of claim 18, wherein the feedstock prior to treatment comprises a mixture solution of about 8-12% dry weight in an aqueous solution.

20. The method of claim 1, wherein the method decreases relative viscosity of the feedstock by at least 50% as compared to the starting material and/or extracts at least about 40% of fermentable sugars found in the feedstock.

21. The method of claim 20, wherein the fermentable sugars comprise one or more of xylose, galactose, and arabinose.

22. The method of claim 1, wherein said method extracts fermentation inhibitors from said feedstock in an amount less than 1% of the volume of the incubation mixture formed by the mixture of feedstock with cellulase.

23. The method of claim 22, wherein the fermentation inhibitors comprise one or more of furfural, hydroxymethylfurfural, formate, and acetate.

24. A method of decreasing the relative viscosity of feedstock comprising:

incubating the feedstock with about 0.50 FPU to about 5 FPU cellulase/g dry weight of feedstock cellulase for about 15 minutes to about 2 hours; wherein the feedstock is incubated at a pH of about 3 or less at a temperature of at least 60° C. and the feedstock, prior to treatment, has a relative viscosity of at least 20,000 cP;

thereby decreasing the relative viscosity of the feedstock and the relative viscosity after treatment is less than 1500 cP.

25. A method of reducing the viscosity of a feedstock having a viscosity of at least 20,000 cP comprising:

combining the feedstock having a viscosity of at least 20,000 cP with a feedstock obtained by treating a feedstock by the method of claim 1, wherein the feedstock having a viscosity of at least 20,000 cP comprises 30% or less of the volume of the feedstock treated by the method of claim 1.

* * * * *